(12) United States Patent
Leiboff

(10) Patent No.: US 11,510,677 B1
(45) Date of Patent: Nov. 29, 2022

(54) LOOP OSTOMY DEVICE

(71) Applicant: Arnold R Leiboff, Old Field, NY (US)

(72) Inventor: Arnold R Leiboff, Old Field, NY (US)

(*) Notice: Subject to any disclaimer, the term of this patent is extended or adjusted under 35 U.S.C. 154(b) by 537 days.

(21) Appl. No.: 16/693,698

(22) Filed: Nov. 25, 2019

Related U.S. Application Data

(63) Continuation-in-part of application No. 15/643,197, filed on Jul. 6, 2017, now abandoned.

(60) Provisional application No. 62/854,481, filed on May 30, 2019, provisional application No. 62/359,147, filed on Jul. 6, 2016.

(51) Int. Cl.
 *A61B 17/12* (2006.01)
 *A61F 5/449* (2006.01)

(52) U.S. Cl.
 CPC ........ *A61B 17/12013* (2013.01); *A61F 5/449* (2013.01)

(58) Field of Classification Search
 CPC ... A61B 17/12009–12013; A61B 2017/12018; A61F 5/445–449; A61F 2005/4495
 See application file for complete search history.

(56) References Cited

U.S. PATENT DOCUMENTS

| | | | |
|---|---|---|---|
| 3,779,247 A | 12/1973 | Nolan et al. | |
| 4,067,339 A | 1/1978 | Chiulli | |
| 4,465,486 A | 8/1984 | Hill | |
| 4,671,272 A | 6/1987 | Steer | |
| 4,828,553 A | 5/1989 | Nielsen | |
| 5,026,361 A | 6/1991 | Matysiak | |
| 5,356,391 A | 10/1994 | Stewart | |
| 5,456,246 A | 10/1995 | Schmieding et al. | |
| 5,549,619 A | 8/1996 | Peters et al. | |
| 5,803,902 A * | 9/1998 | Sienkiewicz | A61B 17/0218 128/853 |
| 5,941,860 A | 8/1999 | Wheeler | |
| 6,443,959 B1 * | 9/2002 | Beland | A61B 17/32002 606/127 |
| 6,716,209 B2 | 4/2004 | Leiboff | |
| 7,896,848 B2 | 3/2011 | Charukhchian | |
| 2003/0163121 A1 | 8/2003 | Leiboff | |
| 2009/0318854 A1 | 12/2009 | Bailey | |
| 2010/0292540 A1 | 11/2010 | Hess et al. | |

OTHER PUBLICATIONS

Hollister, Loop Ostomy Bridge, downloaded Nov. 25, 2019.

* cited by examiner

*Primary Examiner* — Thaddeus B Cox
(74) *Attorney, Agent, or Firm* — Brian Roffe

(57) ABSTRACT

Loop ostomy device including an elongate rod having expanded end portions is restrained beneath an exteriorized loop of bowel by retaining elements that can be removably passed over a portion of the rod to a position in proximity to the bowel. In methods of use, the loop ostomy device, after being deployed through the bowel mesentery, and after maturation of the stoma, is inserted along with the open bowel through the aperture of an ostomy appliance wafer that is fixed to the body wall and into the pouch of the appliance.

20 Claims, 13 Drawing Sheets

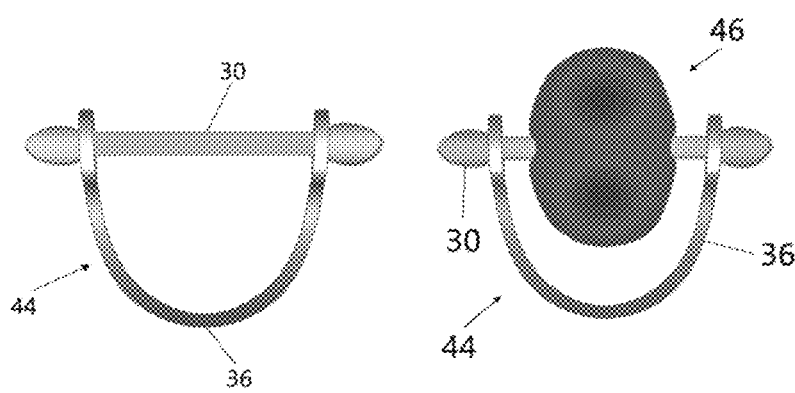

LOOP OSTOMY DEVICE

CROSS-REFERENCE TO RELATED APPLICATIONS

This application claims priority of U.S. provisional patent application Ser. No. 62/854,481 filed May 30, 2019, and is a continuation-in-part of U.S. patent application Ser. No. 15/643,197 filed Jul. 6, 2017, now abandoned, which claims priority of U.S. provisional patent application Ser. No. 62/359,147 filed Jul. 6, 2016, all of which are incorporated by reference herein.

FIELD OF THE INVENTION

The invention relates generally to devices used for abdominal surgery, and more particularly, the invention relates to a loop ostomy device used to maintain a portion of the bowel outside of the body and to methods using such a device.

BACKGROUND OF THE INVENTION

Some abdominal surgery operations require a loop of the bowel to be maintained temporarily or permanently outside the body. These procedures are generally referred to as loop ostomies, such as a loop colostomy or a loop ileostomy, because a loop of bowel is pulled through an incision in the abdominal wall. In such a procedure, a pouch or similar container is fixed to the skin over the bowel via an adhesive-backed wafer. The pouch and wafer, which are either made as a one-piece integral unit or as a two-piece assembly comprised of a wafer with a flange and a pouch with a flanged open end, are commonly referred to as an ostomy appliance.

In order to maintain the eviscerated loop of bowel in position, and prevent it from retracting into the abdomen while healing, devices are used to secure the bowel, which are generally known as rods or bridges. One such device was distributed under the trademark SUR-FIT® by ConvaTec Inc. It is substantially the same as the device described in U.S. Pat. No. 4,671,272. Prior art FIGS. 1-5 illustrate a portion of the loop ostomy procedure utilizing the SUR-FIT® Loop Ostomy Rod from ConvaTec.

Referring now to prior art FIG. 1, the SUR-FIT® Loop Ostomy Rod is a rigid rod 10 that has a fixed cross-piece 12 at one end and a rotatable cross-piece 14 at the other end. Before installing the rod 10, the rotatable cross-piece 14 is rotated to the position shown in FIG. 1.

After the abdomen is incised and a loop of bowel is exteriorized, the rod 10 is inserted through the mesentery 15 of the bowel 16 as shown in prior art FIG. 2. The rotatable cross-piece 14 is then rotated to the position shown in prior art FIG. 3 so as to prevent the rod 10 from sliding free under the highly slippery surface of the bowel 16.

With the rod 10 in position, a hole 18 is cut in a wafer 20 as shown in prior art FIG. 4. Adhesive backing is removed from the wafer 20; it is then positioned over the stoma; and the rod 10 is carefully manipulated so that it lies on top of the wafer 20 within a flange 22 as shown in prior art FIG. 5. Other (not illustrated) steps in the procedure include incising the bowel 16 and coupling the pouch (not shown) to the flange 22 of the wafer 20.

The dimensions of the rod 10 and the diameter of the flange 22 are dictated by the diameter of the exteriorized bowel. Thus, several different size appliances and rods are typically needed since different patients with different-sized exteriorized bowel loops require different-sized rods. In many instances, it is deemed prudent to secure the rod with stitches despite the presence of the cross-pieces 12, 14.

Another device is distributed under the trademark EASY LOOP™ by Tools for Surgery, LLC, East Setauket, N.Y. and described in U.S. Pat. No. 6,716,209 (FIG. 6) The device is comprised of an eight-inch long 0.28" diameter semiflexible tube 102, with an arrow-shaped slotted coupling member 104, 106 on each end of the tube 102. The arrow-shaped coupling members 104, 106 allow for an easy insertion through the mesentery. FIG. 7 shows the EASY LOOP™ already threaded through the mesentery and coupled together forming the closed loop. Both the arrow shaped coupling members 104, 106 and the formation of a loop are means to prevent the device from being dislodged and the bowel from sliding back into the body.

Other devices marketed as loop ostomy devices include the loop colostomy bridge from Hollister Inc., which is described in U.S. Pat. No. 3,779,247, and loop ostomy rods from Marlen Manufacturing and Development Co., which includes the version shown in FIG. 8. These commercially available rods are often sutured to the skin to prevent dislodgement.

Other apparatus and techniques have been used to secure bowel loops at or above the surface of the abdominal wall. The article "Securing the Loop-Historic Review of the Methods Used for Creating a Loop Colostomy" (Dis Colon Rectum. 191 November; 34(11):1014-21) describes many of these techniques. Among other identified information, this article illustrates three commercial devices and six alternative methods. This article and the other patent literature mentioned herein are incorporated by reference herein.

One method that this article illustrates for securing the bowel loop above the surface of the skin incorporates a rigid rod 200 and a rubber tube 201, FIG. 9. The two ends of the tube are fitted over respective ends of the rod in order to maintain the rigid rod in position. The expanded diameter of the tube end over the rod ends prevent the rod from slipping out of its position under the bowel.

OBJECTS AND SUMMARY OF THE INVENTION

It is an objective of at least one embodiment of the invention to provide a loop ostomy device.

Another objective of at least one embodiment of the invention is to provide a family of loop ostomy devices that are usable with exteriorized bowel segments of various calibers and with various appliance sizes.

Still another objective of at least one embodiment of the invention is to provide a loop ostomy device which is secured without the need for stitches.

Yet another objective of at least one embodiment of the invention is to provide a loop ostomy device which is easy to use, apply and remove, and which affords and allows facile replacement of the ostomy appliance while the device is maintained in situ.

Still another objective of at least one embodiment of the invention is to provide a loop ostomy device which is inexpensive to manufacture.

Still another objective of at least one embodiment of the invention is to provide a loop ostomy device that maintains the open bowel above skin level.

It is still another objective of at least one embodiment of the invention to provide a method of using a loop ostomy device which is secure without the need for stitches.

It is still another objective of at least one embodiment of the invention to provide a method of using a loop ostomy device that maintains the open bowel above skin level.

In order to achieve one or more of these objectives, a loop ostomy device of the present invention includes a substantially rigid rod and a flexible strap. A family of loop ostomy devices are provided that are usable with exteriorized bowel segments of various calibers and with various appliance sizes. In an exemplifying use, the rod is positioned beneath the exteriorized bowel loop. Each end of the strap is fitted on a respective end of the rod in order to maintain the rod in position beneath the bowel loop.

BRIEF DESCRIPTION OF THE DRAWINGS

The invention, together with further objects and advantages thereof, may best be understood by reference to the following description taken in conjunction with the accompanying drawings wherein like reference numerals identify like elements.

FIG. 13 illustrates the arrangement of the strap on the rod according to the invention.

FIG. 14 depicts the deployment of the device according to the invention, securing a loop of bowel above skin level.

DETAILED DESCRIPTION OF THE INVENTION

Figure 10:
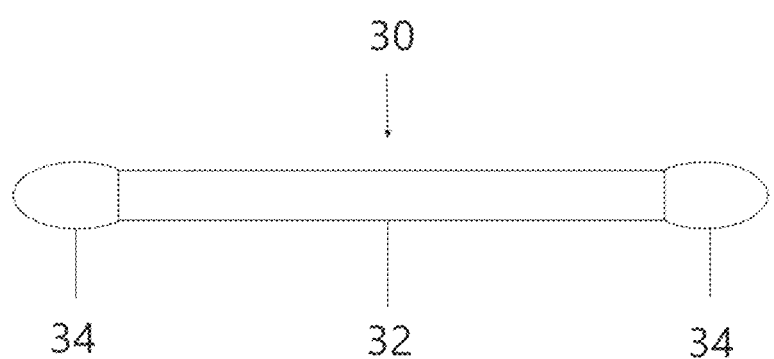
FIG. 10 illustrates a top view of the rod of a first embodiment of this invention.

Referring to the accompanying drawings wherein like reference numbers refer to the same or similar element, turning initially to FIG. 10, a first embodiment of the rod component of an assembly of the present invention comprises a substantially rigid rod 30 having a central elongate cylindrical portion 32 and expanded ovoid end portions 34. Central portion 32 has a substantially uniform cross-sectional shape of a circle between its opposite ends and may be, as shown, straight in an unstressed condition. The ovoid end portions 34 can have a maximum thickness greater than the maximum thickness of the central portion 32. Also, a central axis of the rod 30 passes through the central portion 32 and the ovoid end portions 34 so that the rod 30 may be symmetrical about the central axis along its entire length. Instead of a central elongate cylindrical portion, the central elongate portion may have a cross-sectional shape of an oval, or flat oval. Instead of expanded ovoid end portions, the end portions may be spherical, or substantially conical, flat conical, rhomboid, diamond, heart or arrow shaped.

Rod 30 may be made of various plastic materials, such as Delrin. One skilled in the art would readily appreciate that the rod 30 may be made of different materials, whether homogeneous or a composite of multiple materials. In one size, the dimensions of the rod 30 are selected to provide a suitable retention of the bowel, e.g., with a total length of about 3.0 inches and a thickness along the central axis of from about 0.2 inches to about 0.35 inches. The central portion 32 has a length of about 2.2 inches so that the length of each expanded end portion is about 0.4 inches. Multiple different sizes of the rod 30 are contemplated.

Figures 11, 12:
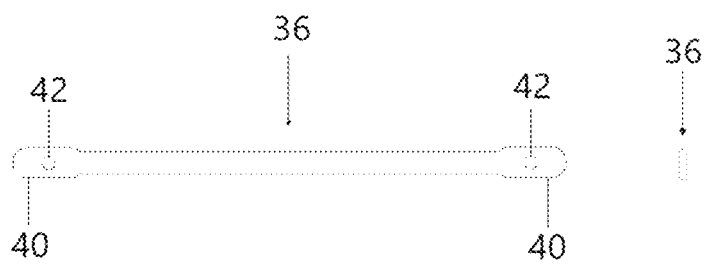
FIG. 11 illustrates a top view of the strap of a first embodiment of this invention.
FIG. 12 illustrates an end view of the strap of a first embodiment of this invention.

Referring now to FIGS. 11 and 12, a first embodiment of the strap of the present invention comprises a flexible elastomeric strap 36 having a central elongate portion 38, that may be planar or cylindrical, with expanded planar end portions 40. By the end portions 40 being expanded, it is meant that their width, when viewed as shown in FIG. 11, is greater than the width of the central elongate portion 38, with the expansion being on both sides of the central elongate portion 38. By the end portions 40 being planar, it is meant that that have opposed surfaces, e.g., a front surface and a rear surface, that are substantially parallel to one another to provide the expanded end portions 40 with a uniform thickness and flat major surfaces. The front surface of the expanded end portions 40 is contiguous with the front surface of the elongate portion 38 while the rear surface of the expanded end portions 40 is contiguous with the rear surface of the elongate portion 38. Thus, the strap 36 may have a uniform thickness throughout.

A second embodiment of the strap of this invention would be an elongate elastomeric strap with uniform width, without expanded ends. The strap is not a tube in that it is not required to have a hollow interior between its extreme ends, and with an opening at each end leading to the hollow interior. At a minimum, the end portions 40 are planar and do not include an axial opening.

Rather, end portions 40 each contain an aperture 42 extending through the body of the end portions 40 from a front surface to a rear surface and through which, in use, ovoid end portions 34 of rod 30, are passed through to form assembly 44 illustrated in FIG. 13. As such, the dimensions of the apertures 42 are selected in consideration of the dimensions of the ovoid end portions 34. As shown, apertures 42 are circular but this is not intended to limit the invention. The combination of the ovoid end portion 34 of the rod 30 and the aperture 42 of the end portion 40 of the strap 36 may be considered as coupling means that removably couple the ovoid end portion 34 and the end portion 40 together. These coupling means are integral with the rod 30 and strap 36, i.e., no additional coupling or connecting structure is required to provide for a secure engagement of the ovoid end portion 34 to a respective end portion 40. Also, such coupling means do not include structure which does not extend entirely through an aperture to pass between opposed surfaces of the member defining the aperture and thereby be partly situated outward of both surfaces of the member defining the aperture.

Strap 36 may be made of silicone with a durometer of about 60 Shore A. One skilled in the art would readily appreciate that different properties of the strap 36 are also possible, e.g., different materials whether a single material or a combination of materials, different hardness, and different finishes for the outer surface. In one embodiment, the dimensions of the strap 36 are selected to provide a convenient and minimally obstructive placement on the patient, e.g., with a total length of about 5.0 inches and a thickness along the central axis of about 0.63 inches. The elongate portion 38 has a length of about 3.5 inches so that the length of each expanded end portion is about 0.75 inches. The width of the elongate portion 38 is about 0.2 inches and the width of the expanded end portion 40 is about 0.38 inches.

For an exemplifying deployment of the assembly 44, as illustrated in FIG. 14, the deployer first selects a size of the assembly 44, e.g., from sizes including small, medium and large, appropriate for the size of the bowel. Then, one ovoid end portion 34 of rod 30 is passed at least partly through aperture 42 of one end portion 40 of the strap 36 to cause a part of the rod 30 to be situated outward from each surface of the end portion 40 of the strap 36. The opposite end portion 34 of rod 30 is passed through bowel mesentery adjacent an exteriorized loop of bowel 46, and then the free end of rod 30 is passed at least partly through aperture 42 of the free end of strap 36 to cause a part of the rod 30 to be situated outward from each surface of the end portion 40 of the strap 36. The result is that the assembly 44 encircles part of the bowel 46. The rod 30 may be adjusted in its position beneath the exteriorized loop of the bowel, and the ostomy is matured. In this deployment, the central portion 32 of rod 30 is restrained from slipping out from beneath the bowel 46 by the end portions 40 of the strap 36 which are not easily separated from the ovoid end portions 34 of the rod 30. The assembly 44 and bowel may then be arranged within an ostomy appliance.

An exemplifying, non-limiting method of use for the invention includes maturing the stoma by opening the bowel and sewing cut edges to edges of incised skin, cutting an aperture in the wafer of an ostomy appliance, passing the loop ostomy device and bowel through the aperture of the wafer, fixing the wafer to the skin surrounding the stoma, and, if utilizing a two-piece appliance, securing the flange of the pouch to the flange of the wafer. The loop ostomy assembly is removed when the bowel becomes fixed in place by healing. In order to remove the assembly, one end of the strap 36 is pulled off the rod 30 by passing end portion 34 of rod 30 back through aperture 42 of the respective end portion 40 of the strap 36, and withdrawing rod 30 from under the bowel.

Figure 15:
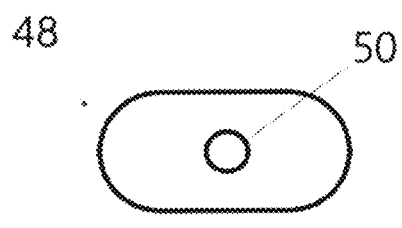
FIG. 15 illustrates a top view of a retaining element according to a second embodiment of this invention.

A second embodiment of the invention comprises elastomeric planar geometric forms with apertures, such as retaining element 48 with aperture 50 illustrated in FIG. 15, instead of a strap, as the retaining elements through which the rod is passed, one such retaining element placed on either side of the bowel. As such, the dimensions of the aperture 50 in each retaining element 48 are selected in consideration of the dimensions of the ovoid end portions 34 of the rod 30. As shown, the aperture 50 is circular but this is not intended to limit the invention. Also, the retaining element 48 is shown with a particular cross-sectional shape, e.g., straight upper and lower edges and curved side edges, but this illustrated shape also does not limit the retaining elements 48 as they can have various shapes as would be evident to those skilled in the art to which this invention pertains (see, for example, FIG. 16 described below).

For an exemplifying deployment of the assembly using two retaining elements 48, one ovoid end portion 34 of the rod 30 is passed through aperture 50 of one retaining element 48, the opposite ovoid end portion 34 of rod 30 is passed through bowel mesentery adjacent an exteriorized loop of bowel, and then the free end of the rod 30 is passed through aperture 50 of another retaining element 48, so that the assembly has two retaining elements 48, one on each side of the bowel 46. In this deployment, the central portion 32 of rod 30 is restrained from slipping out from beneath the bowel by the retaining elements 48.

Figure 16:
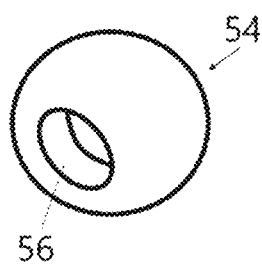
FIG. 16 illustrates a perspective view of a retaining element according to a third embodiment of this invention.

A third embodiment of the invention comprises more three-dimensional forms, such as a ring 54 with an aperture 56 shown in FIG. 16, as the retaining elements through which the rod 30 is passed. As such, the dimensions of the aperture 56 in the ring 54 are selected in consideration of the dimensions of the ovoid end portions 34 of the rod 30. As shown, the aperture 56 is circular, forming a tubular channel in the ring 54, but this is not intended to limit the invention.

Ring 54 functions in substantially the same way as retaining element 48. The outer surface of the ring is curved when viewed in cross-section through a central axis of the ring 54. Ring 54 may be made of silicone with a durometer of about 50 Shore A. One skilled in the art would readily appreciate that different properties of the ring 54 are also possible, e.g., different materials whether a single material or a combination of materials, different hardness, and different finishes for the outer surface. In one size, the dimensions of the ring 54 are selected to provide a convenient and minimally obstructive placement on the patient, e.g., with a diameter of about 0.5 inches and a thickness along the central axis of about 0.25 inches.

As mentioned above, it is an objective of the invention to provide a family of loop ostomy devices that are usable with exteriorized bowel segments of various calibers and with various appliance sizes. To this end, the assembly 44, whether comprising rod 30 and strap 36, or comprising rod 30 and a pair of retaining elements 48, or comprising rod 30 and a pair of rings 54, can be made in different sizes. For example, this means that the rod 30 can be manufactured in a variety of different configurations, including, but not limited, different lengths in total, different combinations of the length of the elongate portion 32 and the length of the expanded end portions 34, as well as different diameters of the elongate portion 32 and the expanded end portions 34 and different shapes of the expanded end portions 34. The strap 36 can also be made in different sizes, as well as the retaining elements 48 and the rings 54.

As also mentioned above, an objective of the invention is to provide a loop ostomy device which is secured without the need for stitches. A surgeon or other medical personnel securing the assembly 44 only has to insert the end portions 34 of the rod 30 through apertures in either the flexible strap 36, when its end portions 40 are manipulated to be on opposite sides of the bowel (the embodiment of FIGS. 10-14), or two retaining elements 48 positioned on opposite sides of the bowel (the embodiment of FIG. 15), or two rings 54 positioned on opposite sides of the bowel (the embodiment of FIG. 16). The strap or retaining elements secure the rod in place, and there is no need to stitch the rod to the skin.

Also, it is recognized that the rod 30 is a separate component from the strap 36. The strap 36 therefore has several positions relative to the rod 30, namely, a first (sale or preparatory) position in which it is not engaged at all with the rod 30, a second (temporary) position in which one of the end portions 40 has an expanded end portion 34 of the rod 30 passing therethrough, and a third (use) position in which both end portions 40 have a respective end portion 34 of the rod 30 passing therethrough and the strap 36 is flexed around the exteriorized loop of bowel The ends of the strap 36 thus include rod-retaining structure configured to be positioned on both sides of an eviscerated bowel loop such that movement of the rod 30 is restrained and the rod 30 is, during use of assembly 44, maintained in position under the loop of bowel. The ends of the strap 36, or other retaining elements, restrict movement of the rod 30, so that the ends of the rod 30 protrude out from opposite sides of the bowel, and the ends of the rod 30 sit on or above skin, and neither end of the rod 30 is drawn under the bowel. As such, the bowel is prevented from retracting into the tissues of the abdominal wall and abdominal cavity, and it can be securely retained above skin level.

Figure 1:
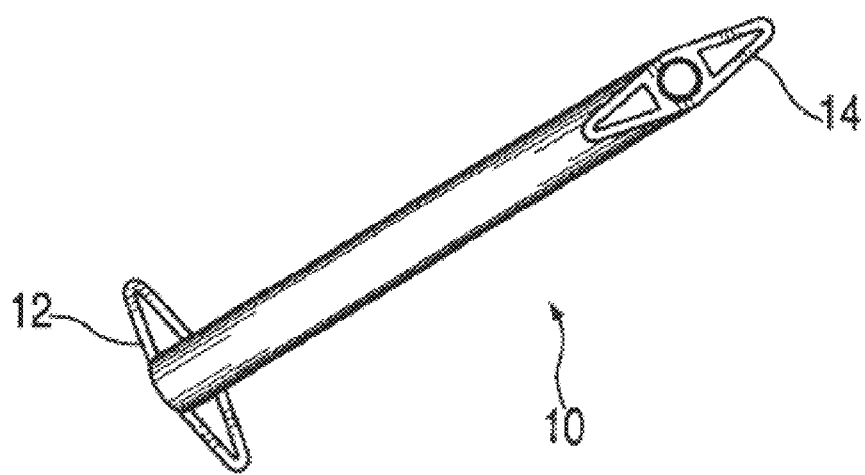
FIG. 1 is a top view of a first prior art ostomy device.
Figure 2:
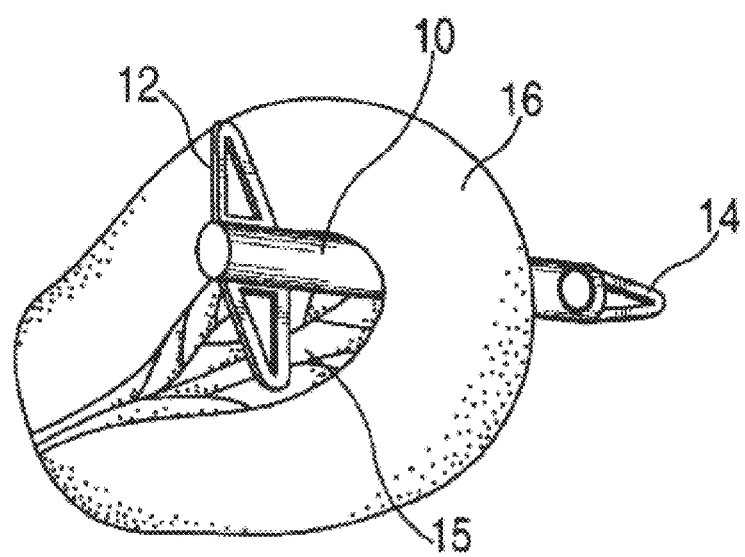
FIGS. 2-5 illustrate how the first prior art ostomy device is used.
Figure 3:
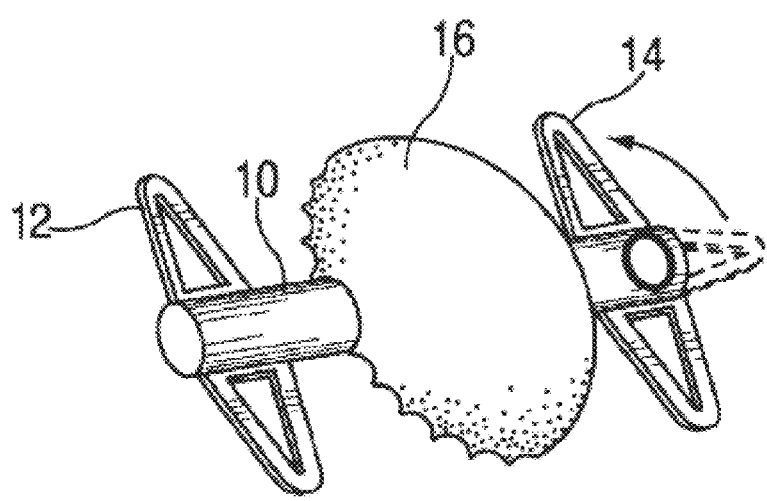
Figure 4:
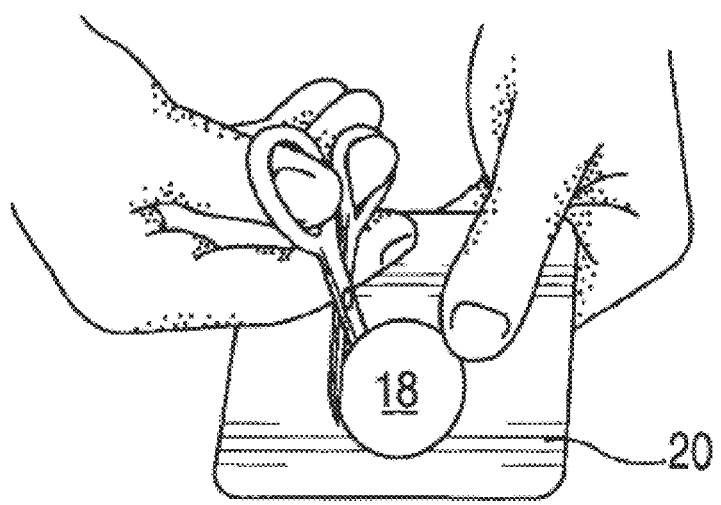
Figure 5:
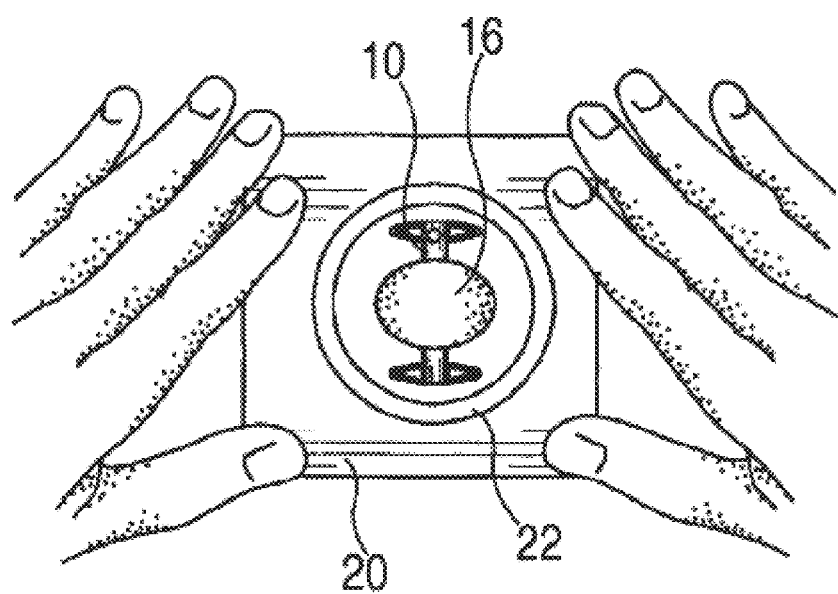
Figure 6:
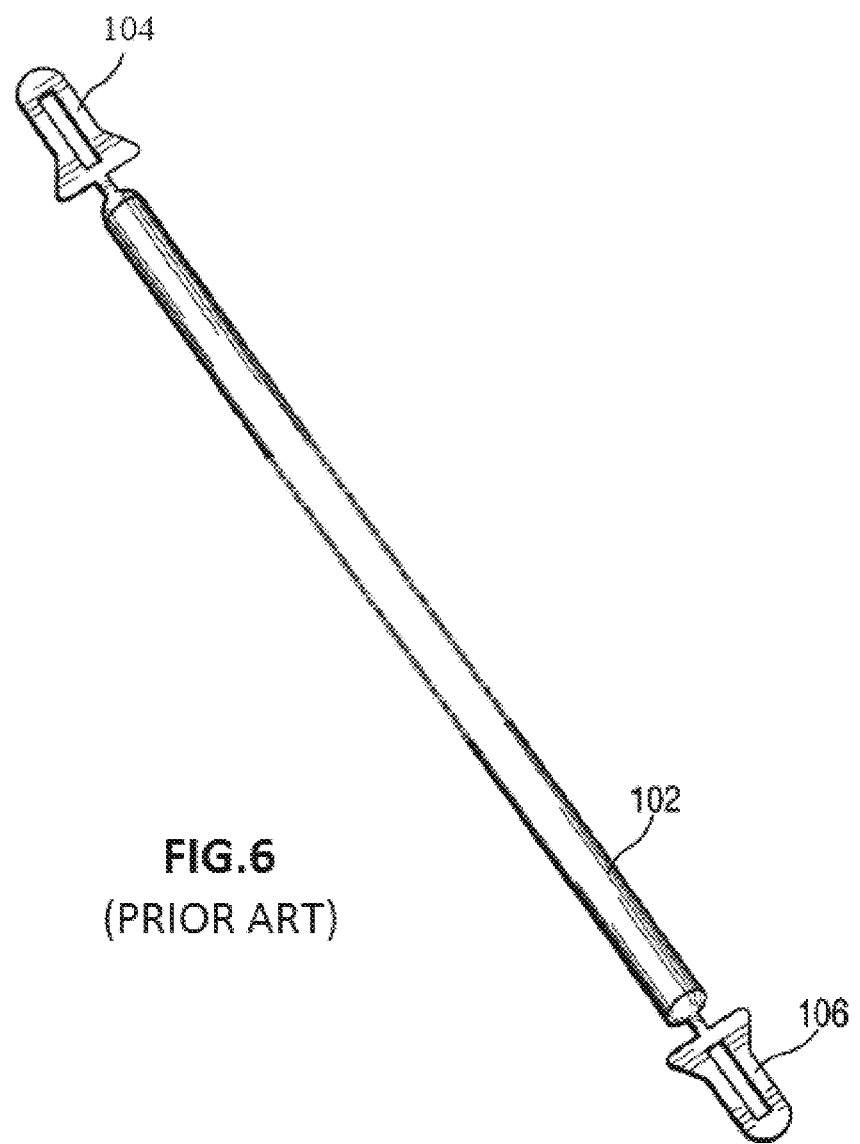
FIG. 6 is a top view of a second prior art ostomy device.
Figure 7:
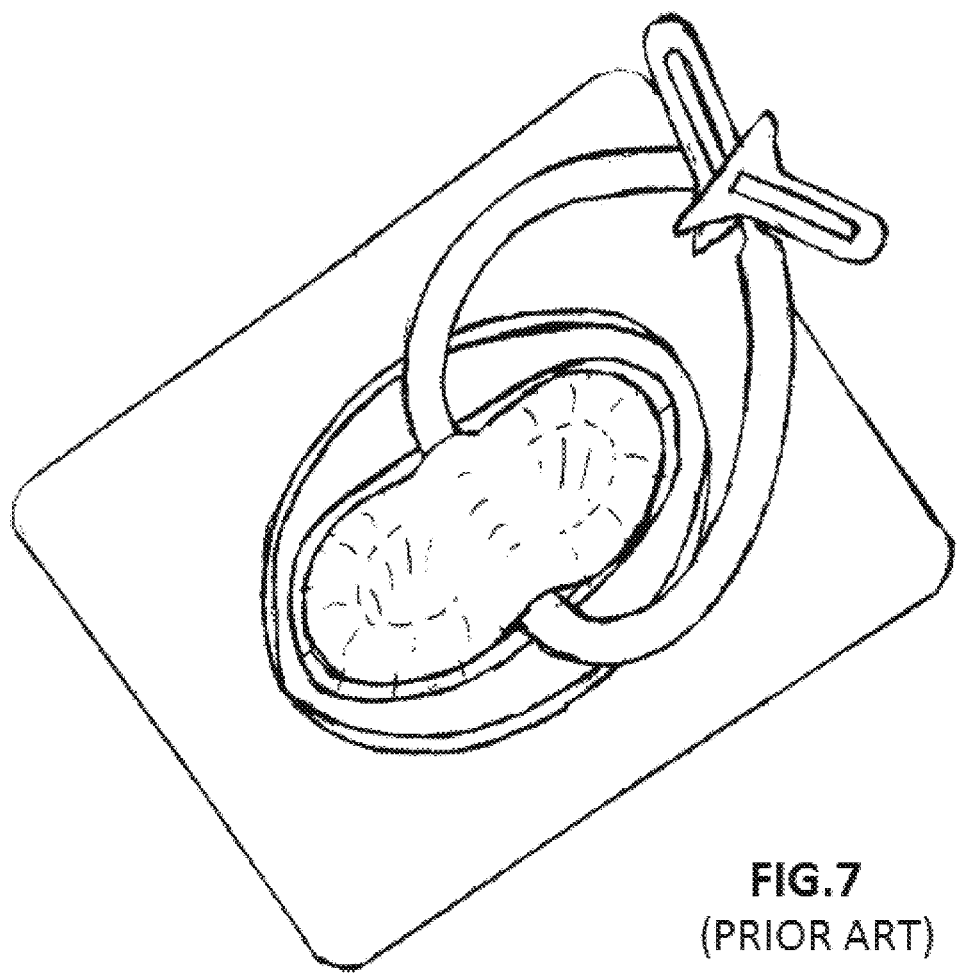
FIG. 7 illustrates how the second prior art ostomy device is used.
Figure 8:
FIG. 8 illustrates a third prior art ostomy device.
Figure 9:
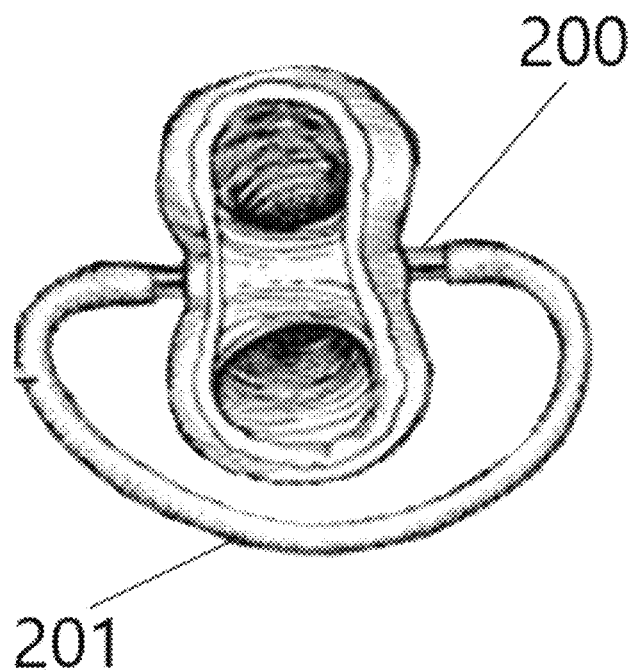
FIG. 9 illustrates a fourth prior art device and how it is used.

Another feature of the invention that warrants discussion is the fact that the strap 36 is not connected to itself around the bowel (in contrast to the EASY LOOP™ device illustrated in FIGS. 6 and 7). Rather, in the assembly of the invention, there is a plurality of separated components, whether the rod 30 and strap 36, or the rod 30 and two retaining elements 48 or the rod 30 and two rings 54. These separated components are manufactured independently, but with the intention that they will cooperate with one another.

Another important feature of the invention that must be appreciated is that the expanded end portions 34 of the rod 30 entirely extend through the apertures 42 on the end portions 40 of the strap 36 (as well as the apertures 50 on the retaining elements 48 and the apertures 56 on the rings 54), to the extent that most if not all of the expanded end portions 34 of the rod 30 would be situated on one side of the planar end portion 40 while the elongate section 32 of the rod 30 is situated on an opposite side of the planar end portion 40 in the installed state of the assembly 44. This passage of the expanded end portion 34 of the rod 30 and its consequent extension beyond the aperture 42 provides a more secure coupling of the rod 30 and strap 36, preventing dislodgment of the bowel. The same feature prevents expanded end portion 34 or rod 30 from slipping under the bowel, which could result in retraction of the bowel into or through the abdominal wall.

While particular embodiments of the invention have been shown and described, it will be obvious to those skilled in the art that changes and modifications may be made without departing from the invention in its broader aspects, and, therefore, the aim in the appended claims is to cover all such changes and modifications as fall within the true spirit and scope of the invention. Further, particular features of any of the disclosed embodiments may be used in any other of the disclosed embodiments to the extent possible.

The invention claimed is:

1. A bowel retaining device, comprising:
   a rigid rod having first and second expanded end portions;
   a flexible strap separate and apart from said rod and having first and second end portions;
   first coupling means for removably coupling said first end portion of said strap and said first expanded end portion of said rod together; and
   second coupling means for removably coupling said second end portion of said strap and said second expanded end portion of said rod together,
   whereby said rod and said strap are engagable with one another to enable at least part of a bowel to be retained therebetween.

2. The device of claim 1, wherein said first and second expanded end portions have an ovoid shape.

3. The device of claim 1, wherein said first and second expanded end portions have a spherical shape.

4. The device of claim 1, wherein said first and second expanded end portions have a conical shape.

5. The device of claim 1, wherein said first and second end portions of said strap which couple to said first and second expanded end portions of said rod, respectively, are planar.

6. The device of claim 1, wherein said first and second coupling means are integral with said rod and said strap.

7. The device of claim 1, wherein said first and second end portions of said strap have opposed front and rear surfaces, said first end portion of said strap comprising an aperture extending from said front surface to said rear surface to enable one of said first and second expanded end portions of said rod to pass at least partly therethrough and cause part of said rod to be positioned outward from both of said front and rear surfaces of said first end portion, and said second end portion of said strap comprising an aperture extending from said front surface to said rear surface to enable another of said first and second expanded end portions of said rod to pass at least partly therethrough and cause part of said rod to be positioned outward from both of said front and rear surfaces of said second end portion.

8. The device of claim 1, wherein said first and second end portions of said strap each comprise an aperture through which a respective one of said first and second expanded end portions of said rod passes to thereby cause engagement of said strap and said rod.

9. The device of claim 8, wherein said first and second end portions of said strap comprise retaining elements configured to be positionable on both sides of an eviscerated bowel loop such that, when positioned as such, movement of said rod is restrained and said rod is maintained in position under the eviscerated bowel loop.

10. The device of claim 8, wherein said apertures are circular.

11. The device of claim 1, wherein said rod has an elongate cylindrical portion between said first and second expanded end portions.

12. The device of claim 11, wherein said rod is configured such that a central axis of said rod passes through said elongate cylindrical portion between said first and second expanded end portions, and through said first and second expanded end portions.

13. The device of claim 1, wherein said rod is symmetrical about a central axis along its entire length.

14. The device of claim 1, wherein said rod is made of plastic.

15. The device of claim 1, wherein said strap has an elongate portion between said first and second end portions.

16. The device of claim 15, wherein said elongate portion of said strap is planar.

17. The device of claim 16, wherein said first and second end portions of said strap are planar and have opposed front and rear surfaces, said front surfaces of said first and second portions of said strap being contiguous with a front surface of said elongate portion of said strap and said rear surfaces of said first and second portions of said strap being contiguous with a rear surface of said elongate portion of said strap on an opposite side of said elongate portion of said strap from said front surface of said elongate portion of said strap.

18. The device of claim 1, wherein said strap has a uniform thickness.

19. The device of claim 1, wherein said strap is made of silicone.

20. The device of claim 1, wherein a length of said strap is greater than a length of said rod.

* * * * *